United States Patent [19]

Hill et al.

[11] Patent Number: 4,946,988

[45] Date of Patent: Aug. 7, 1990

[54] PROCESS FOR THE PREPARATION OF α-L-ASPARTYL-L-PHENYLALANINE METHYL ESTER HYDROCHLORIDE BY USE OF ISOLATED N-FORMYL L-ASPARTIC ANHYDRIDE

[75] Inventors: John B. Hill, Woodstock; Yefim Gelman, Arlington Hts., both of Ill.

[73] Assignee: The NutraSweet Company, Deerfield, Ill.

[21] Appl. No.: 219,613

[22] Filed: Jul. 14, 1988

[51] Int. Cl.$^5$ ............................................. C07C 101/02
[52] U.S. Cl. ...................................... 560/41; 562/450
[58] Field of Search .......................... 560/41; 562/450; 260/546

[56] References Cited

U.S. PATENT DOCUMENTS

| | | |
|---|---|---|
| 3,933,781 | 1/1976 | Bachman et al. |
| 4,745,210 | 5/1988 | Mita et al. ............................... 560/41 |
| 4,820,861 | 4/1989 | Yukawa et al. ........................ 560/41 |

*Primary Examiner*—Bruce Gray
*Attorney, Agent, or Firm*—Jeffrey M. Hoster; John M. Sanders

[57] ABSTRACT

A process for the preparation of α-L-aspartyl-L-phenylalanine methyl ester hydrochloride (α-APM(HCl)) is disclosed. α-APM(HCl) is an intermediate in the preparation of aspartame.

26 Claims, No Drawings

PROCESS FOR THE PREPARATION OF α-L-ASPARTYL-L-PHENYLALANINE METHYL ESTER HYDROCHLORIDE BY USE OF ISOLATED N-FORMYL L-ASPARTIC ANHYDRIDE

BACKGROUND OF THE INVENTION

The present invention relates to a method for the preparation of alpha(α)-L-aspartyl-L-phenylalanine methyl ester hydrochloride (α-APM(HCl)) which is used to prepare α-L-aspartyl-L-phenylalanine methyl ester (α-APM), a sweetening agent which is approximately 200 times sweeter than sucrose. The potency of this compound, a dipeptide, enables one to sweeten foods and beverages using a far lesser amount than one could with sugar. Consequently, it has enabled millions of consumers to reduce their caloric intake while not having to give up the sweet things in life. It also lacks the unpleasant aftertaste associated with other sweeteners such as saccharin and cyclamate. Additionally, the present invention relates to a method of increasing the α/B ratio of APM (HCl) and methods of producing a reaction mixture of N-formyl-α-L-aspartyl-L-phenylalanine (FAP) having a stirrable viscosity.

α-APM is not new and was described in U.S. Pat. 3,492,131 to Schlatter in 1970. Numerous other patents involving different methods of manufacture and related compounds have since issued and much literature has been written heralding the effect the dipeptide has had on the low calorie sweetener industry. Up until the present time, however, the methods of preparation have involved costly isolation and recovery processes which consequently must be shouldered by the consumer. The present invention is a method of preparation having the operational simplicity of a one-pot process as well as improved yields of the desired end product.

α-L-aspartyl-L-phenylalanine methyl ester is a dipeptide composed essentially of two amino acids, L-aspartic acid and L-phenylalanine. It has been known for some time that the sweetening property of the dipeptide is dependent upon the stereochemistry of these individual amino acids. Each of these amino acids can exist in either the D or L form, and it has been determined that the L-aspartyl-L-phenylalanine esters are sweet while the corresponding D-D, D-L and L-D isomers are not. Combinations of the isomers which contain the L—L dipeptide, DL-aspartyl-L phenylalanine, L-aspartyl DL-phenylalanine and DL-aspartyl-DL phenylalanine are sweet, but only half as sweet since the racemate contains ½ of the L—L moiety.

The dipeptide is produced through a coupling reaction in which L-aspartic acid is joined with L-phenylalanine or its methyl ester. This coupling reaction requires an amino protecting group attached to the aspartic acid moiety such as formyl, acetyl, acetoacetyl, benzyl, substituted and unsubstituted carbobenzoxy, t-butoxy carbonyl and the hydrohalide salt. The amino protecting group, often referred to in the art as the N-protecting group, for purposes of this disclosure shall be referred to as N-formyl since the formyl moiety is the blocking agent of the present invention. N-formyl aspartic anhydride is a widely used starting material and its process has been described extensively. See U.S. Pat. No. 4,173,562.

However, obtaining isolated N-formyl aspartic anhydride has resulted in relatively low yields when a large excess of formic acid is used as solvent. A twofold excess of formic acid, for example, creates the need for addition of toluene or other solvents to reduce anhydride solubility, thereby requiring extensive solvent recovery steps.

The coupling reaction is carried out in a solvent and is a common step in several patented processes for the production of α-L-aspartyl-L-phenylalanine methyl ester (α-APM); see U.S. Pat. No. 3,962,207 to Uchiyama, U.S. Pat. No. 4,173,562 to Bachman and EPO Patent 127,411 to Yaichi et al., all of which are incorporated herein by reference. During the coupling reaction of the two amino acids, two isomers are produced as intermediates and their stereochemistry ultimately determines the sweetness of the particular molecule. The alpha (α) isomer is the desired product in that isolated fractions of pure α-APM possess a sweetness about 130–200 times that of sugar. The beta (β) isomer fraction, however, has no such sweetness.

This invention is directed to improvements in the preparation of α-APM (HCl) which result in lower costs of production and increased yields of the β isomer which is the desired end product.

The α and β isomers of APM are given below:

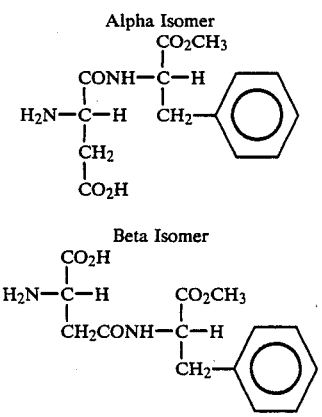

It has been determined that formation of the α and β isomers and their respective ratios from the coupling reaction depends upon what kind of solvent is used to carry out the reaction, the temperature at which the reaction occurs and the quantity of the solvents used. According to U.S. Pat. No. 4,173,562 to Bachman, an α/β isomer ratio of 75:25 is achievable when acetic acid is used as a solvent in the coupling reaction at 50° C. The molar ratio of acetic acid to phenylalanine must be at least 10:1. The α/β isomer ratio drops considerably to 69/31 when the acetic acid to L-phenylalanine molar ratio is reduced to 6:1. The present invention shows that the α/β ratio can be increased to about 80/20 if the acetic acid, used as a solvent in the coupling reaction is partially replaced with an alkyl ester, hindered alcohol or mixture thereof. For purposes of this disclosure, hindered alcohol as it is used herein shall mean a secondary or tertiary alcohol.

A problem that resides with the use of these solvents in this process is that after 0.5–3 hours of reaction time, the reaction mixture solidifies and becomes substantially difficult to agitate, concentrate, deformylate, or remove from a reactor. A stirrable system is necessary for at least two reasons. First, stirring ensures a mixing of the reactants to achieve a complete reaction. Secondly, solvent must later be removed by distillation.

Another problem that exists in the prior art is that under some techniques, 25% or more of the α-APM is lost because it remains in the original reaction solution. See U.S. Pat. No. 4,173,562. A further problem is that in the '562 patent, N-formyl-L-aspartic anhydride is produced from a reaction mixture of aspartic acid, a large excess of formic acid and acetic anhydride. The excess amount of formic acid must at some point be removed by distillation and separated from acetic acid which adds to the cost of the final product.

U.S. Pat. No. 3,962,207 describes a similar process in which L-aspartic anhydride hydrochloride is coupled with L-phenylalanine methyl ester. A problem that arises in the '207 process is that a large amount of L-phenylalanine methyl ester is required which adds to the cost of the process. Secondly, that results in the formation of significant amounts of tri-peptides which must be removed and thereby necessitate expensive and elaborate separation techniques. This is not required in the present invention.

U.S. Ser. No. 156,268 describes a one-pot process for preparation of α-APM in which reaction by-products which result from the formation of formylated L-aspartic anhydride also serve as the solvent for the coupling reaction with L-phenylalanine.

SUMMARY OF THE INVENTION

The present invention is directed to a process to prepare α-APM(HCl). This is a process whereby N-formyl-L-aspartic anhydride is formed and isolated from reaction by-products prior to the coupling with L-phenylalanine. This isolation is completed by filtering the N-formyl-L-aspartic anhydride to remove excess formic acid. Since the amount of formic acid used is minimized, additional solvents to decrease N-formyl-L-aspartic anhydride solubility are not needed. Increased yields of α-APM (HCl) are afforded by use of the isolated N-formyl-L-aspartic anhydride. Diluting the coupling reaction with an ester or hindered alcohol is also disclosed as effective in the present case to improve the yield of α-APM (HCl).

Initially, N-formyl-L-aspartic anhydride is prepared by combining aspartic acid with acetic anhydride and formic acid in a reaction process similar to that known in the art. See U.S. Pat. Nos. 3,933,781, 3,962,207 and 4,173,562. The present invention, however, utilizes a minimal amount of formic acid (1.33–1.35 Molar equivalents per mole of aspartic acid) and the excess formic acid can be removed by one of numerous methods such as filtration or centrifugation.

The N-formyl aspartic anhydride can then be suspended or dissolved in acetic acid and coupled by adding L-phenylalanine (L-Phe). An alkyl ester or hindered alcohol is optionally added to the coupling reaction and surprisingly improves the α/β ratio. Whereas an ester is normally prepared by reacting an alcohol with an anhydride, it is unexpected that the hindered alcohol does not attack the N-formyl aspartic anhydride during the course of the reaction. Acetic acid is also added to provide a solvent for the reaction. This coupling reaction can be conducted under low or no agitation conditions to keep the viscosity of the reaction mixture low resulting in a stirrable final reaction mixture.

The resulting dipeptide is then concentrated by distillation and deformylated with HCl and esterified by adjusting the concentrations of methanol, water and HCl to amounts effective to produce a high yield of α-APM(HCl). The α-APM(HCl) precipitates from the reaction mixture and is isolated and neutralized with a base to form α-APM.

DESCRIPTION OF THE INVENTION

The present invention relates to an improved process for preparing α-APM(HCl). The process begins by mixing L-aspartic acid with a minimal amount of formic acid (at least 1.33 Molar equivalents based on aspartic acid) and acetic anhydride (at least about 2.0 Molar equivalents based on aspartic acid) in the presence of a catalyst such as magnesium oxide resulting in the formation of N-formyl-L-aspartic anhydride. Suitable catalysts include oxides, hydroxides and salts of metals and are disclosed in U.S. Pat. Nos. 4,508,912 and 4,550,180 which are incorporated herein by reference. This reaction is conducted at temperatures up to about 52° C. The mixture is preferably stirred at about 50° C. for at least about 2.5 hours, and preferably for about 6 hours. The amount of formic acid used is preferably 1.33 to 1.35 Molar equivalents based on aspartic acid.

The final reaction mixture is then cooled to 10° C.–20° C., and the resulting solid is isolated. Isolation may be completed by centrifugation or filtration and washing with acetic acid. The solid N-formyl-L-aspartic anhydride is isolated, with acetic acid possibly left in the mixture. The isolated anhydride is added to an alkyl ester or a hindered alcohol or suitable mixture of the two and additional acetic acid. The resulting slurry is then reacted with L-phenylalanine, preferably in equimolar amounts.

It has been found that the alkyl ester and/or hindered alcohol increase the α/β ratio when added in an amount equivalent to at least about 1.2 moles per mole of L-phenylalanine. The α/B ratio increases with increasing amounts of ester or alcohol up to a point where the molar amount of ester, alcohol or combinations thereof is approximately 4.7 times that of L-phenylalanine. At this point, a saturation level is reached wherein the isomer ratio remains constant regardless of how much more ester or alcohol is added.

Preferably, the alkyl ester utilized in the coupling reaction is selected from the group comprising methyl acetate, ethyl acetate, isopropyl acetate, n-butyl acetate and isopropyl formate. Methyl acetate (MeOAc) is a preferred alkyl ester. If methyl acetate is used, the amount added should be 1.2 to 4.7 times the amount of L-phenylalanine on a mole/mole basis. Hindered alcohols that may be used include isopropyl alcohol and secondary or tertiary butyl alcohol. Isopropyl alcohol is a preferred hindered alcohol. These are the preferred embodiments of the invention and are by no means intended to restrict the use of other alkyl esters or hindered alcohols nor is this intended to limit the scope of this invention.

The coupling reaction is then carried out by stirring the aforementioned mixture for about 4–6 hours at a temperature between about 0°–60° C., and preferably between 15°–40° C. One problem that develops during the coupling reaction is that as the reaction takes place with the formation of N-formyl-L-aspartyl-L-phenylalanine, the mixture or slurry begins to solidify, i.e. increase in viscosity, to the point where stirring becomes extremely difficult if not impossible. High viscosity to this extent makes agitation very difficult and inhibits heat transfer which prevents distillation of acetic acid, esters and/or hindered alcohol described below. It has been discovered that the acetic acid which was added just prior to or during the coupling reaction inhibits this solidification, i.e. the viscosity is lowered. This is important in that mixing insures completion of the reaction. Moreover, the acid and esters must be removed from the mixture by distillation prior to deformylation. The reaction mixture must be stirrable in order to efficiently complete the reaction.

The amount of acetic acid added depends upon how much N-formyl-L-aspartic anhydride was synthesized. If the N-formyl-L-aspartic anhydride is isolated by filtration in the presence of acetic acid, some acetic acid may already be present. The total amount of acetic acid in the system should be about 6 to 16 times that of L-phenylalanine on a mole/mole basis, preferably about 11.1 times that of L-phenylalanine on a mole/mole basis. Therefore, one would not necessarily add acetic acid in an amount 11.1 times that of the L-phenylalanine that is added. A lesser amount wherein the total molar amount of acetic acid present in the system is about 11.1 times that of the L-phenylalanine is sufficient.

Another unique aspect of the present invention involves the lowering of the viscosity of the coupling reaction mixture by controlling the agitation of the coupling reaction mixture. It has been discovered that stopping or lowering the speed of the agitator during the coupling reaction dramatically causes a lowering of the viscosity of the coupling reaction mixture. In a large reactor (10 feet diameter reactor fitted with a mechanical stirrer having 5 foot long paddles, very slow agitation, such as 5–40 revolutions per minute (rpm), and occasional agitation, such as, briefly running the agitator every 5–15 minutes, drastically reduce the viscosity of the coupling reaction mixture when compared to reactions conducted with an agitator speed of about 60 or more rpm. In lab scale reactors (4 inch round bottom flask with 3 inch paddles) 200–300 rpm causes a very thick reaction mixture while agitation at 5–15 rpm produces a very stirrable low viscosity reaction mixture. Also, turning off the agitator after about 1 hour after the L-Phe has been added to the reaction mixture and restarting it after the reaction, i.e., after about 6 hours, produces a reaction mixture with a low viscosity. However, in a commercial scale operation where the agitator is stopped for periods over 1 hour it can be very difficult to restart the agitator because of settling and caking of the precipitate. Therefore, slow agitation and periodic agitation are preferred.

When used herein the terms "stirrable" or "low viscosity" when referring to the coupling reaction mixtures, mean a liquid which can be stirred or poured in a glass or reactor vessel. Such liquids generally have a viscosity of under about 15,000 Centipoise (cp), advantageously between 1,000–10,000 cp, and preferably between 150–500 cp.

The means of agitation are not critical in the practice of the present invention. Any standard agitation means can be employed; i.e., injection of an inert gas, shaking, tumbling the reactor, mechanical stirrers, etc. Mechanical stirrers are preferred. The exact stirrer configuration is not critical either. With paddle or blade stirrers, the stirrer speed is advantageously set at from about 5 to about 40 rpm and preferably at about 20 rpm. While the paddle tip speed in meters/second (m/sec) will vary at a set rpm based on the paddle length, it has been found that rpm is more accurate description of the agitator speed in the practice of the present invention. Any stirrer speed under about 40 rpm is acceptable in reducing the viscosity of the reaction mixture. However, it should be noted that in lab scale equipment (4 in. flask) a stirrer speed between 40–150 rpm will produce a stirrable reaction mixture.

The $\alpha$ and $\beta$ isomers of N-formyl-$\alpha$-L-aspartyl-L-phenylalanine ($\alpha/\beta$ F-AP) produced by the above-described invention can be analyzed by high performance liquid chromatography (HPLC) and will show that these processes yield an unusually high $\alpha/\beta$ ratio of approximately 79.5:20.5.

Optionally, acetic acid and any esters (methyl acetate, isopropyl formate, etc.) or hindered alcohol are removed from the reaction mixture prior to the deformylation step described below. Preferably, the acetic acid and esters are vacuum distilled at from about 15 to about 25 inches of mercury. The vacuum distillation is conducted prior to the addition of HCl employed to deformylate the $\alpha/\beta$ F-AP. The acetic acid, esters and/or alcohol are recovered and recycled for use in subsequent coupling reactions.

The $\alpha$ and $\beta$ isomers of N-formyl-L-aspartyl-L-phenylalanine are then deformylated. Hydrochloric acid, and optionally methanol, are added to the isomer mixture in order to deformylate the $\alpha/\beta$ F-AP resulting in formation of $\alpha/\beta$-AP. Excess methanol also reacts with any left over acetic acid and formic acid present in the reaction mixture to yield methyl acetate and methyl formate which have much lower boiling points than acetic acid or formic acid and thereby can be removed from the system by distillation at lower temperatures.

The resulting mixture of $\alpha/\beta$-AP and their various methyl esters is then esterified by adjusting the concentration of HCl, methanol and water to amounts sufficient to produce a high yield of $\alpha$-APM(HCl). The methanol concentration should be from about 1 to about 10 weight percent and preferably from about 3 to about 5 weight percent. The HCl concentration should be from about 9% to about 18% by weight and preferably from about 12.5% to about 14.5% by weight. The water concentration should be from about 32 to about 50 weight percent and preferably from about 37 to about 42 weight percent. After the concentrations of water, HCl and methanol have been adjusted accordingly, the reaction mixture is gently agitated at temperatures under about 35° C. and preferably at ambient temperature (20°–30° C.). The esterification is complete in about 4 to about 10 days and usually in about 6 days.

The resulting hydrochloride salt of $\alpha$-L-aspartyl-L-phenylalanine methyl ester ($\alpha$-APM(HCl)) is then easily separated from the $\beta$ isomer since $\alpha$-APM.HCl.2H$_2$O has a lower solubility in aqueous solutions than $\beta$-APM(HCl). See U.S. Pat. No. 3,798,207 to Ariyoshi. The $\alpha$ isomer precipitates from solution and is separated by filtration, centrifugation, decantation or one of many other conventional methods.

The $\alpha$-APM(HCl) is then neutralized with a base to form APM which is then recovered by crystallization techniques well known in the art.

The following examples are provided to specifically demonstrate the invention at hand. These examples are set forth by way of illustration only and it is intended that the invention is not to be construed as being limited either in spirit or in scope by the details contained herein as modifications in both. The materials and methods will be apparent from this disclosure to those skilled in the art.

EXAMPLE 1

Magnesium oxide (0.121 grams; 0.003 mole) was dissolved in 19.3 grams (0.4 mole) of 95% formic acid under nitrogen. Acetic anhydride (69.3 grams; 0.655 mole) was then added to the solution which was stirred for 10–15 minutes. The temperature of the mixture rose to 40° C. L-aspartic acid (39.93 grams; 0.30 mole) was added to the mixture and the resulting slurry was stirred at about 50° C. for about 6 hours. N-formyl-L-aspartic anhydride was formed at this point as shown by high performance liquid chromatography (HPLC). The mixture was then filtered and washed with 30 grams of acetic acid in order to isolate the N-formyl-L-aspartic anhydride. The yield of the N-formyl-L-aspartic anhydride from the L-aspartic acid was 80%. The N-formyl-L-aspartic anhydride will include some acetic acid, which remains for use as a solvent in the coupling step.

Methylacetate(46.35 grams; 49.8 ml) and acetic acid (159.8 grams, 152.1 ml.) were added to the N-formyl-L-aspartic anhydride (41.1 grams, including 4.36 grams of acetic acid). L-phenylalanine (39.65 grams, 0.24 mole) was added to the above mixture, which was stirred at about 25° C. for about 5 hours. HPLC analysis showed N-formyl-L-aspartyl-L-phenylalanine having about 78% of the $\alpha$ isomer and about 22% of the $\beta$ isomer. The mixture was distilled under 20" of Mercury vacuum at 60°–73° C. to remove 120 ml of solvents. Methanol (58.5 ml.) and 35% HCl (26.7 ml.) were added to the N-formyl-L-aspartyl-L-phenylalanine, and the mixture was heated to 60° C. and agitated for 30 minutes. The mixture was distilled at atmospheric at a temperature of about 70°–75° C. in order to remove methyl formate and methylacetate. Distillation was continued while an additional 108 ml. of methanol was added. The distillation continued at atmospheric pressure until the temperature reached 85° C. and then a vacuum was applied until the temperature decreased to 30° C. Hydrochloric acid (32.4 ml.), water (21.7 ml.), and methanol (9 ml) were added, and the mixture was stirred for six days at room temperature (22°–27° C.) during which time the hydrochloric salt of $\alpha$-L-aspartyl-L-phenylalanine methyl ester formed and precipitated. Saturated brine (50 ml.) was used to wash the product. The product, white crystalline $\alpha$-L-aspartyl-L-phenylalanine methyl ester hydrochloride dihydrate, weighed 58.8 grams and contained 72% by weight of $\alpha$-L-aspartyl-L-phenylalanine, a 60% yield based on the starting quantity of L-phenylalanine.

EXAMPLE 2

N-formyl-L-aspartic anhydride was isolated by filtering and washing with acetic acid. Different alkyl esters and hindered alcohols were used as solvents in varying amounts in order to determine the effect of esters and alcohols other than methyl acetate in $\alpha/\beta$ isomer ratios. The different esters and alcohols are listed in Table 1 with the quantities used, as well as the $\alpha/\beta$ isomer ratio obtained by use of each solvent.

N-formyl-L-aspartic anhydride (28.6 grams; 0.20 mole) was slurried with 100 ml. of acetic acid and 0.90 moles of the particular cosolvent under a nitrogen atmosphere. L-phenylalanine (33.04 grams; 0.20 moles) was added to each respective reaction mixture which was then rinsed with 20 ml. of additional acetic acid. Each mixture was stirred at room temperature (22°–27° C.) for approximately five hours. As the coupling reactions moved toward completion, the slurries became thicker and more voluminous. Each slurry was then heated to about 50° C. for one hour and a 10:1 mixture of methanol and water was added until all solids were dissolved. Each mixture was weighed and 1 gram aliquots were withdrawn and analyzed by HPLC. The $\alpha/\beta$ ratios yielded by use of each solvent are listed in Table 1.

TABLE 1

| Solvent | Quantity | Alpha/Beta ratio |
| --- | --- | --- |
| Methyl Acetate | 71.5 ml | 79:21 |
| Ethyl Acetate | 88.0 ml | 80:20 |
| Isopropyl Acetate | 105.5 ml | 81:19 |
| n-Butyl Acetate | 118.5 ml | 81:19 |
| Methyl Formate | 55.5 ml | 76:24 |
| Isopropyl Formate | 71.0 ml | 78:22 |
| Isopropyl Alcohol | 69.0 ml | 77:23 |
| sec-Butyl Alcohol | 82.5 ml | 78:22 |
| tert-Butyl Alcohol | 85.0 ml | 79:21 |
| Acetic Acid alone | 51.5 ml | 76:24 |

EXAMPLE 3

N-formyl-L-aspartic anhydride was prepared according to the procedure set forth in Example 1 and was isolated from the initial reaction mixture by filtering and washing with acetic acid. 13.3 Grams (0.1 mole) of N-formyl-L-aspartic anhydride was mixed with 34.41 grams (0.405 mole) of methyl acetate followed by the addition of 14.57 grams (0.09 mole) of L-phenylalanine to the mixture. After stirring for approximately 3 hours, the slurry was left overnight at room temperature (20°–25° C.). The resulting mixture was dissolved in a 9:1 mixture of methanol and water. The $\alpha/\beta$ isomer ratio of the N-formyl-L-aspartyl-L-phenylalanine was 80:20 by HPLC.

What is claimed is:

1. A method of preparing $\alpha$-APM hydrochloride, which comprises the steps of:
   (a) formylating L-aspartic acid in a reaction mixture of formic acid and acetic anhydride to yield N-formyl-L-aspartic anhydride;
   (b) isolating said N-formyl-L-aspartic anhydride;
   (c) coupling said N-formyl-L-aspartic anhydride with L-phenylalanine at an effective temperature, said coupling carried out in the presence of an amount of added acetic acid sufficient to reduce the viscosity of said reaction mixture so that said reaction mixture is stirrable and in the presence of a suitable amount of an alkyl ester, a hindered alcohol or mixture thereof, to yield $\alpha$, $\beta$-N-formyl-L-aspartyl-L-phenylalanine isomers;
   (d) deformylating said isomers by adding an effective amount of hydrochloride acid.
   (e) removing residual acetic acid and formic acid from the reaction mixture;
   (f) esterifying the deformylated isomers by adding an effective amount of methanol, water, and hydrochloric acid to the reaction mixture to yield $\alpha$- and $\beta$-APM hydrochloride wherein the $\alpha$-APM hydrochloride precipitates; and
   (g) isolating the $\alpha$-APM hydrochloride.

2. The method of claim 1
   wherein the coupling step (c) further comprises vacuum distilling acetic acid, hindered alcohol and esters present in the reaction mixture prior to the deformylation step (d);
   the deformylation step (d) further comprises the addition of an amount of methanol effective to esterify any formic acid and acetic acid present in the reaction mixture; and
   step (e) includes the removal of the resulting methyl acetate and methyl formate.

3. The method of claim 2 wherein the removal step (e) is conducted by atmospheric distillation.

4. The method of claim 3 wherein the removal step (e) is conducted by vacuum distillation.

5. The method of claim 2 further comprising neutralizing the isolated α-APM hydrochloride with a base to form APM.

6. The method of claim 2 wherein the total molar amount of acetic acid present is at least 6 times that of L-phenylalanine.

7. The method of claim 6 wherein the total molar amount of acetic acid present is about 11 times that of L-phenylalanine.

8. The method of claim 2 wherein the alkyl ester is added in step (c) in a molar amount of at least 1.2 times that of L-phenylalanine.

9. The method of claim 8 wherein the alkyl ester is methyl acetate, ethyl acetate, isopropyl acetate, n-butyl acetate, isopropyl formate or mixtures thereof.

10. The method of claim 2 wherein the hindered alcohol is added to step (c) in a molar amount of at least 1.2 times that of L-phenylalanine.

11. The method of claim 10 wherein the hindered alcohol is isopropyl alcohol, secondary butyl alcohol, tertiary butyl alcohol or mixtures thereof.

12. The method of claim 2 wherein said mixture of alkyl ester and hindered alcohol is added to step (c) in a molar amount of at least 1.2 times that of L-phenylalanine.

13. The method of claim 2 wherein the coupling step (c) is conducted in the absence of agitation.

14. The method of claim 2 wherein the coupling step (c) is conducted under agitation conditions sufficient to form a final reaction mixture which is stirrable.

15. The method of claim 14 wherein the agitation is achieved with a mechanical stirrer.

16. The method of claim 15 wherein the mechanical stirrer is revolved at less than about 40 revolutions per minute (rpm).

17. The method of claim 15 where the mechanical stirrer is run periodically throughout the reaction.

18. The method of claim 14 wherein said agitation conditions comprise:
 (a) vigorous agitation for about the first ½ hour after the addition of L-phenylalanine; and
 (b) slow or intermittent agitation thereafter.

19. The method of claim 16 wherein the agitation is achieved with a mechanical stirrer and:
 (a) vigorous agitation is achieved at a stirrer speed of about 60 rpm,
 (b) slow agitation is achieved at a stirrer speed of about 20 rpm, and
 (c) intermittent agitation is achieved by running the stirrer at least once every 15 minutes for at least 1 minute.

20. A method for preparing α-APM hydrochloride which comprises:
 (a) formylating L-aspartic acid in a first reaction mixture of formic acid and acetic anhydride to yield N-formyl-L-aspartic anhydride;
 (b) isolating said N-formyl-L-aspartic anhydride;
 (c) coupling said N-formyl-L-aspartic anhydride with L-phenylalanine in the presence of (i) acetic acid and (ii) a suitable amount of an alkyl ester, a hindered alcohol or mixture thereof, at a temperature of from about 5° C. to about 40° C. to yield α,β-N-formyl-L-aspartyl-L-phenylalanine isomers;
 (d) vacuum distilling acetic acid and methyl acetate from the reaction mixture;
 (e) deformylating said isomers by adding effective amounts of HCl and methanol;
 (f) vacuum distilling formic acid and acetic acid from the reaction mixture;
 (g) esterifying the deformylated isomers by adding effective amounts of methanol and HCl to the reaction mixture to yield α,β-APM-hydrochloride wherein the α-APM-hydrochloride precipitates; and
 (h) isolating the α-APM-hydrochloride.

21. The method of claim 20 wherein (1) the molar ratio of acetic acid to L-phenylalanine is at least about 11 to 1 and (2) methanol is added to the reaction during the vacuum distillation step (f) in amounts effective to facilitate the removal of acetic acid and formic acid by forming the corresponding methyl esters.

22. The method of claim 21 wherein the molar ratio of hindered alcohol, alkyl ester or mixtures thereof to L-phenylalanine is at least about 1.2:1.

23. The method of claim 22 wherein the alkyl ester is methyl acetate, ethyl acetate, isopropyl acetate, n-butyl acetate, isopropyl formate or mixtures thereof.

24. The method of claim 22 wherein the hindered alcohol is isopropyl alcohol, secondary butyl alcohol, tertiary butyl alcohol or mixtures thereof.

25. The method of claim 21 wherein the coupling step (c) is conducted under agitation conditions sufficient to form a final reaction mixture which is stirrable.

26. The method of claim 24 wherein the agitation is achieved with a mechanical stirrer at a speed of less than about 30 rpm.

* * * * *